United States Patent
Frantz

(10) Patent No.: US 10,564,169 B2
(45) Date of Patent: Feb. 18, 2020

(54) METHODS FOR THE DIAGNOSIS, CONTROL AND PROPHYLAXIS OF INFLAMMATION AND MITIGATION OF INFLAMMATORY CONDITIONS IN CANINES

(75) Inventor: Nolan Zebulon Frantz, Andover, NJ (US)

(73) Assignee: Colgate-Palmolive Company, New York, NY (US)

( * ) Notice: Subject to any disclaimer, the term of this patent is extended or adjusted under 35 U.S.C. 154(b) by 233 days.

(21) Appl. No.: 13/642,576

(22) PCT Filed: May 5, 2011

(86) PCT No.: PCT/US2011/035429
§ 371 (c)(1),
(2), (4) Date: Oct. 22, 2012

(87) PCT Pub. No.: WO2011/143048
PCT Pub. Date: Nov. 17, 2011

(65) Prior Publication Data
US 2013/0041024 A1    Feb. 14, 2013

Related U.S. Application Data

(60) Provisional application No. 61/334,084, filed on May 12, 2010.

(51) Int. Cl.
*G01N 33/50* (2006.01)
*G01N 33/68* (2006.01)

(52) U.S. Cl.
CPC .................. *G01N 33/6893* (2013.01)

(58) Field of Classification Search
CPC .... A61K 31/202; A61K 31/355; A61K 8/678; G01N 2800/105
See application file for complete search history.

(56) References Cited

U.S. PATENT DOCUMENTS

| | | | |
|---|---|---|---|
| 6,156,355 A * | 12/2000 | Shields et al. | 426/74 |
| 8,148,325 B2 | 4/2012 | Yamka et al. | |
| 8,252,742 B2 | 8/2012 | Yamka et al. | |
| 8,496,981 B2 | 7/2013 | Zicker et al. | |
| 2006/0073192 A1 | 4/2006 | Friesen et al. | |
| 2007/0231371 A1 | 10/2007 | Pan et al. | |
| 2008/0299110 A1* | 12/2008 | Scuderi | 424/130.1 |
| 2009/0111877 A1* | 4/2009 | Yamka et al. | 514/560 |
| 2011/0123669 A1 | 5/2011 | Yamka et al. | |
| 2011/0183006 A1 | 7/2011 | Yamka et al. | |

FOREIGN PATENT DOCUMENTS

| WO | WO 05/110124 | 11/2005 |
|---|---|---|
| WO | WO 2006/002976 * | 1/2006 |
| WO | WO 06/053010 | 5/2006 |
| WO | WO 2006/126008 | 11/2006 |
| WO | WO 07/002837 | 1/2007 |
| WO | WO 07/079301 | 7/2007 |
| WO | WO 10/009458 | 1/2010 |
| WO | WO 10/009474 | 1/2010 |

OTHER PUBLICATIONS

Paetau-Robinson et al ("Foods With Lipoic Acid and Elevated Levels of Vitamin E and Vitamin C Correlate With Whole Blood Antioxidant Concentrations and May Protect Geriatric Dogs From Oxidative Stress." Intern J Appl Res Vet Med, 2006; 6(2):93-100).*
Tagoe et al ("Annexin-1 mediates TNF-a-stimulated matrix metalloproteinase secretion from rheumatoid arthritis synovial fibroblasts." J Immunol 2005; 181:2813-2820.).*
Bieri et al ("Expressing dietary values for fat-soluble vitamins: changes in concepts and terminology" The American Journal of Clinical Nutrition, 1981;34:289-295).*
Toll ("Nutritional Management: Optimal Osteoarthritis Diet" Canine Osteoarthritis: Overview, Therapies, & Nutrition, Apr. 2005 Supplement to NAVC Clinician's Brief, p. 6).*
Kevorkian et al (Arthritis & Rheumatism, 2004; 50(1):131-141).*
Alturfan et al., 2007, "Increased Serum Sialic Acid Levels in Primary Osteoarthritis and Inactive Rheumatoid Arthritis," Tohoku J. Exp. Med. 213(3):241-248.
Frantz et al., 2007, "Identification of Gene Changes in Geriartric Dogs Fed a Test or Control Food," FASEB J. 21(6):705.13 Abstract only.
Frantz et al., 2010, "Effect of Prescription Diet® Canine j/d on Clinical Measures, Cartilage Biomarkers, and Metabolomic Changes in Dogs with Osteoarthritis," J. Vet. Internal Med. 24:718 Abstract #156.
Frantz et al., 2010, "Effect of Prescription Diet Canine j/d on Whole Blood Gene Expression in Dogs with Osteoarthritis," J. Vet. Internal Med. 24:771 Abstract #326.
Gregory et al., 2008, "Dietary Supplements for Osteoarthritis," American Family Physician 77(2):177-184.
Hill's, 2008, Prescription Diet Canine j/d Trockfutter.
Hill's, 2010, "UB0172: Update on Evidence-Based Clinical Nutrition" retrieved from internet http://www.hillsyet.com/conference-documents/Mobility/UB0172_Update_FattyAcids_JointHealth.pdf.
Hill's, 2011, "Osteoarthritis" retrieved from internet http:www.hillsproducts.com/pdfs/jd-en.pdf.

(Continued)

*Primary Examiner* — Marcos L Sznaidman
*Assistant Examiner* — Rayna Rodriguez

(57) ABSTRACT

The invention relates to methods of diagnosis, control and prophylaxis of inflammation and mitigation of inflammatory conditions, particularly arthritis and joint pain, in canines, comprising measuring inflammatory biomarkers wherein elevated levels of the biomarkers in blood correlates to reduced inflammation and reduced levels in blood correlates to increase level in the tissues. The invention further provides a method to treat or control inflammation comprising administering a diet comprising increased levels of one or more of DHA, EPA, vitamin C, vitamin E, and/or L-carnitine.

9 Claims, No Drawings

(56) References Cited

OTHER PUBLICATIONS

International Search Report and Written Opinion in International Application No. PCT/US09/051169, dated Oct. 6, 2009.
International Search Report and Written Opinion in International Application No. PCT/US11/035429, dated Nov. 17, 2011.
Mateescu et al., 2005, "Increased MIG-6 mRNA Transcripts in Osteoarthritic Cartilage," Biochem. Biophys. Res. Comm. 332:482-486.
Shikhman et al., 2005, "Chondroprotective Activity of N-Acetylglucosamine in Rabbits with Experimental Osteoarthritis," Ann. Rheum. Dis. 64(1):89-94.
Written Opinion in International Application No. PCT/US11/035429, dated Mar. 30, 2012.
Yushi Yuryo Handobukku, 1988, (Temporary English title: "Handbook of Fats and Oils"), Saiwai Shobo Co., Ltd., 1st Edition 1st Issue, pp. 482-483 w/ partial English translation.
"Canine Osteoarthritis: The emerging role of nutritional management," Clinical Edge, Oct. 2004.
Roush et al., 2010, "Multicenter Veterinary Practice Assessment of the Effects of Omega-3 Fatty Acids on Osteoarthritis in Dogs," Journal of the American Veterinary Medical. Association 236(1):59-66.

\* cited by examiner

METHODS FOR THE DIAGNOSIS, CONTROL AND PROPHYLAXIS OF INFLAMMATION AND MITIGATION OF INFLAMMATORY CONDITIONS IN CANINES

CROSS-REFERENCE TO RELATED APPLICATIONS

This application is a national stage entry under 35 U.S.C. § 371 of International Patent Application No. PCT/US2011/035429, filed May 5, 2011, which claims priority to U.S. Provisional Patent Application No. 61/334,084, filed May 12, 2010, the entireties of which are incorporated herein by reference.

FIELD OF THE INVENTION

The invention relates to methods of diagnosis, control and prophylaxis of inflammation and mitigation of inflammatory conditions, particularly arthritis and joint pain, in canines, comprising measuring inflammatory biomarkers wherein elevated levels of the biomarkers in blood correlates to reduced inflammation and reduced levels in blood correlates to increased levels in the tissues. The invention further provides a method to treat or control inflammation comprising administering a diet comprising increased levels of one or more of DHA, EPA, vitamin C, vitamin E, and/or L-carnitine.

BACKGROUND OF THE INVENTION

Degenerative joint disease, more often associated with osteoarthritis, is one of the most common musculoskeletal diseases in canines. Biochemically, osteoarthritis is the loss of balance between synthesis and degradation of articular cartilage found in synovial joints. This may include inflammation that often involves the synovial membrane. The cycle of inflammation leads to further degradation of the articular surface resulting in pain and lameness. Arthritis is the most common cause of lameness in canines and the incidence has been reported to affect 20% of canines older than 1 year. Arthritis can occur as a result of abnormal loading, trauma, infection/inflammation, and cruciate ligament ruptures. Predisposing factors include age, breed, size, obesity, and genetics. Understanding how expression of cartilage metabolism related genes are altered in canine arthritis may provide useful insight for treating and/or aiding in the management of arthritic conditions.

Osteoarthritis is a chronic, degenerative joint disease that is caused by the progressive inflammation and deterioration of the cartilage, bone, and soft tissue of one or more joints. Rheumatoid arthritis is an autoimmune condition that causes inflammation and damage to the joints. Both are chronic inflammatory conditions. Because the damage to the joints is progressive and largely irreversible, it is desirable to identify and address the inflammatory process proactively. Unfortunately, biomarker expression in blood has proven difficult to correlate with expression in tissue, making diagnosis difficult before the disease leads to severe pain and irreversible tissue damage.

SUMMARY OF THE INVENTION

Surprisingly, in canines, we see an inverse correlation between expression of many inflammatory biomarkers in blood as compared to tissue. The blood levels of the biomarkers are higher when the tissue levels and associated inflammation are reduced. This inverse correlation is unexpected and provides a novel way to assess the presence of inflammation at an early stage.

Thus the invention provides in a first embodiment a method of detecting an inflammatory condition in a canine, comprising measuring blood levels of one or more inflammatory biomarkers, wherein increased expression in blood is correlated with healing and reduced inflammation in the tissue.

In a further embodiment, the invention provides a method of control and/or prophylaxis of inflammation, or mitigation of inflammatory conditions, particularly arthritis and joint pain, in a canine, comprising identifying the condition by measuring lower levels of inflammatory markers in the blood, and administering a diet comprising increased levels of one or more of DHA, EPA, vitamin C, vitamin E, and/or L-carnitine, e.g., for a period of at least two weeks.

DETAILED DESCRIPTION OF THE INVENTION

The diet for use in the methods herein includes for example, a canine diet comprising increased levels of one or more of DHA, EPA, vitamin C, vitamin E, and/or L-carnitine, e.g., comprising DHA+EPA 0.25-5% on a dry weight basis, for example a diet comprising, on a dry weight basis:
DHA +EPA: 0.5-2.5%,
Vitamin C: 75-1000 mg/kg
Vitamin E: 250-1000 mg/kg
L-carnitine: 100-1000 mg/kg for example, a diet having approximately the nutritional composition of the test diet of Example 1, e.g., having ingredients in the approximate amounts identified in Table 1, +/−10% on a dry weight basis.

The biomarkers for inflammation which are increased in blood when reduced in tissue include, for example, one or more biomarkers selected from: IL-6, ADAMTS-4, IFNG, HAS2, BGN, SOX-9, ADAMTS-5, MMP3, ACP5, ILIA, TNC, HAS3, COMP, IGF-1, GHR, Xaa-Pro Peptidase, RANKL, SMAD7, PGE2, TLR9, PLOD1, and SCL2A9.

EXAMPLE 1

Effect of Diet on Inflammatory Biomarkers in Arthritic Canines

A study was conducted to evaluate the effect of a test diet on selected arthritis related genes in whole blood when fed to canines with osteoarthritis (OA). Thirty-one beagles (initial weight, 13.5±1.27 kg, age, 11.0±2.23 years) with lameness and radiographic changes consistent with OA in at least one joint were included in the study. All canines were fed a control maintenance food for 28 days followed by a test diet containing increased levels of EPA and DHA, Vitamins C and E, and L-carnitine. Whole blood samples were collected on the last day of the control food and after 14 days on test diet. Improved orthopedic exam scores were noted in these canines after 14 days on test diet. After consuming the test formulation for 14 days, OA canines had increased expression of 22 genes (IL-6, ADAMTS-4, IFNG, HAS2, BGN, SOX-9, ADAMTS-5, MMP3, ACP5, ILIA, TNC, HAS3, COMP, IGF-1, GHR, Xaa-Pro Peptidase, RANKL, SMAD7, PGE2, TLR9, PLOD1, and SCL2A9) that were previously demonstrated to be down-regulated in OA versus healthy geriatric canines and decreased expression of ANXA1 that previously was shown to be up-regulated. In summary, feeding test formulation to canines with osteoarthritis resulted in reversal of the gene expression patterns previously observed in the blood of arthritic versus healthy geriatric canines after 14 days.

TABLE 1

Nutritional components of test diet

| Nutrient | Dry Matter |
|---|---|
| Protein (%) | 20 |
| Fat (%) | 16 |
| Carbohydrate (%) | 51 |
| Crude Fiber (%) | 9 |
| Carnitine (mg/kg) | 351 |
| Vitamin C (ppm) | 225 |
| Vitamin E (ppm) | 585 |
| DHA (%) | 0.3 |
| EPA (%) | 0.5 |

The study uses genomic whole blood Nanostring gene analysis to identify changes in selected genes based on previous literature after osteoarthritic canines consumed the test diet.

Thirty-one neutered/ spayed beagles (initial weight, 13.5±1.27 kg, age, 11.0±2.23 years) with varying degrees of radiographic evidence of osteoarthritis and a history of lameness were identified for this study. All canines were otherwise considered healthy by physical exam and serum chemistry profile. All canines were immunized against canine distemper, adenovirus, parvovirus, bordetella, and rabies, and none had chronic systemic disease on the basis of results of physical examination, complete blood count determination, serum biochemical analyses, urinalysis, and fecal examination for parasites. Canines experienced behavioral enrichment through interactions with each other, by daily interaction and play time with caretakers, daily opportunities to run and exercise outside and access to toys. Prior to sample collection, all canines were fed a basal maintenance control food for 28 days. Blood was drawn and collected into PAXgene tubes and stored at −80° C. until evaluation. Genes for analysis were selected based on published literature and those that had available sequences for the canine. Nanostring technology (Expression Analysis) was used to generate data for 89 selected genes.

Genes were normalized based on genes that were most stable across all samples. Genes having a $P<0.05$ (following a false discovery rate adjustment of $Q=0.1$) and a fold-change of at least 1.25 were considered different among the two groups. Up-regulated genes are shown as positive fold-changes. Down-regulated genes are shown as negative fold-changes.

TABLE 2

Effect of test diet on gene regulation after 14 days

| | | Day 14/Day 0 | |
|---|---|---|---|
| Gene name | Gene Symbol | Fold change | P-value |
| Interleukin 6 | IL-6 | 3.2 | 0.01 |
| ADAM metallopeptidase with thrombospondin type 1 motif 4 | ADAMTS-4 | 2.9 | 0.01 |
| Interferon gamma | IFN-gamma | 3.0 | 0.01 |
| Hyaluronic acid synthase 2 | HAS2 | 2.7 | 0.01 |
| Biglycan | BGN | 2.8 | 0.01 |
| Sex determining region Y-box 9 | SOX-9 | 2.8 | 0.01 |
| ADAM metallopeptidase with thrombospondin type 1 motif 5 | ADAMTS-5 | 2.6 | 0.01 |
| Interleukin 1A | IL-1A | 1.7 | 0.01 |

TABLE 2-continued

Effect of test diet on gene regulation after 14 days

| | | Day 14/Day 0 | |
|---|---|---|---|
| Gene name | Gene Symbol | Fold change | P-value |
| Nitric oxide synthase 2A | NOS2A | 2.1 | 0.01 |
| Tenasin C | TNC | 2.1 | 0.01 |
| Hyaluronic acid synthase 3 | HAS3 | 1.9 | 0.01 |
| Cartilage oligomeric matrix protein | COMP | 1.4 | 0.01 |
| Insulin-like growth factor 1 | IGF-1 | 1.4 | 0.01 |
| Ghrelin | GHR | 1.8 | 0.01 |
| Osteonectin | SPARC | 1.8 | 0.01 |
| Peptidase D | PEPD | 1.3 | 0.01 |
| Receptor activator of NF-Kappa B ligand | RANKL | 1.4 | 0.01 |
| SMAD family member 7 | SMAD7 | 1.3 | 0.01 |
| Prostaglandin E2 | PGE2 | 1.5 | 0.01 |
| Toll-like receptor 9 | TLR9 | 1.4 | 0.01 |
| Plasminogen | PLOD1 | 1.4 | 0.01 |
| SCL2A9 Glucose transporter | SCL2A9 | 1.3 | 0.01 |
| Annexin A1 | ANXA1 | −1.3 | 0.01 |
| Fibromodulin | FMOD | 2.5 | 0.01 |
| Hyaluronan and proteoglycan link protein 1 | HAPLN1 | 2.0 | 0.01 |
| Granulocyte-machrophage colony stimulating factor | GM-CSF | 2.3 | 0.01 |
| c-fos induced growth factor (vascular endothelial growth factor D) | FIGF | 2.0 | 0.01 |
| Aggrecan 1 | AGC1 | 2.1 | 0.01 |
| Osteoadherin | OSAD | 1.9 | 0.01 |
| Matrix metalloproteinase 13 | MMP-13 | 2.1 | 0.01 |
| Tumor Necrosis factor-alpha | TNF-a | 1.3 | 0.01 |

Analysis of the whole blood gene expression profiles utilizing the Nanostring technology found differences in 23 of the selected genes between osteoarthritic and normal geriatric canines. Most of these genes are expressed in the opposite direction of that previously reported in osteoarthritic cartilage tissue in canines. However, after osteoarthritic canines consumed the test formulation, the gene expression pattern was reversed to that more like the healthy geriatric canines. This data corroborates the clinical responses measured including improved orthopedic scores and cartilage biomarkers.

The results of the current study showed complete reversal of the selected genes found to be different in osteoarthritic versus normal geriatric canines after consuming the test formulation. In addition to the changes in gene expression, improvements in orthopedic scores and cartilage biomarkers were observed. These may be useful markers to show efficacy of therapeutic foods in canines with OA.

The invention claimed is:
1. A method of treating or controlling osteoarthritis in a canine, the method comprising:
   detecting the osteoarthritis in the canine, wherein detecting the osteoarthritis in the canine comprises measuring decreased levels of one or more osteoarthritis biomarkers and increased levels of ANXA1 (Annexin A1) in blood of the canine as compared to healthy canines, and wherein the decreased levels of the one or more osteoarthritis biomarkers and the increased levels of ANXA1 (Annexin A1) in the blood indicate the presence of the osteoarthritis in tissue of the canine; and
   administering to the canine in need thereof a diet comprising, on a dry weight basis:
      protein: 18-22%;
      fat: 14.4-17.6%;
      carbohydrates: 45.9-56.1%;
      crude fiber: 8.1-9.9%;

DHA: 0.27-0.33%;
EPA: 0.45-0.55%;
Vitamin C: 202.5-247.5 ppm;
Vitamin E: 526.5-643.5 ppm; and
L-carnitine: 315.9-386.1 mg/kg,
wherein the one or more osteoarthritis biomarkers to be measured are one or more of: interleukin 6 (IL-6), a disintegrin and metallopeptidase with thrombospondin type 1 motif 4 (ADAMTS-4), interferon gamma (IFNG), hyaluronic acid synthase 2 (HAS2), biglycan (BGN), sex determining region Y-box 9 (SOX-9), a disintegrin and metallopeptidase with thrombospondin type 1 motif 5 (ADAMTS-5), matrix metalloproteinase 3 (MMP3), acid phosphastase 5 (ACP5), interleukin 1A (IL1A), tenasin C (TNC), hyaluronic acid synthase 3 (HAS3), cartilage oligomeric matrix protein (COMP), insulin-like growth factor 1 (IGF-1), ghrelin (GHR), X-prolyl dipeptidyl aminopeptidase (Xaa-Pro Peptidase), receptor activator of NF-Kappa B ligand (RANKL), mothers against decapentaplegic, drosophila, homolog of SMAD family member 7 (SMAD7), prostaglandin E2 (PGE2), toll-like receptor 9 (TLR9), plasminogen (PLOD1), and SCL2A9 glucose transporter (SCL2A9).

2. The method of claim 1, wherein the diet has the nutritional composition comprising, on a dry weight basis:
Protein: 20%;
Fat: 16%;
Carbohydrate: 51%;
Crude Fiber: 9%;
Carnitine: 351 mg/kg;
Vitamin C: 225 ppm;
Vitamin E: 585 ppm;
DHA: 0.3%; and
EPA: 0.5%.

3. The method of claim 1, wherein decreased levels of the ANXA1 (Annexin A1) levels correlates with reduced osteoarthritis in tissue of the canine.

4. The method of claim 1, wherein the diet is administered to the canine in need thereof for a period of at least two weeks.

5. The method of claim 1 wherein the diet comprises 0.8% of DHA +EPA.

6. The method of claim 1, wherein the one or more osteoarthritis biomarkers to be measured is selected from one or more of: interleukin 6 (IL-6), a disintegrin and metallopeptidase with thrombospondin type 1 motif 4 (ADAMTS-4), interferon gamma (IFNG), hyaluronic acid synthase 2 (HAS2), biglycan (BGN), sex determining region Y-box 9 (SOX-9), a disintegrin and metallopeptidase with thrombospondin type 1 motif 5 (ADAMTS-5), acid phosphastase 5 (ACP5), interleukin 1A (IL1A), tenasin C (TNC), hyaluronic acid synthase 3 (HAS3), insulin-like growth factor 1 (IGF-1), ghrelin (GHR), X-prolyl dipeptidyl aminopeptidase (Xaa-Pro Peptidase), receptor activator of NF-Kappa B ligand (RANKL), mothers against decapentaplegic, drosophila, homolog of SMAD family member 7 (SMAD7), prostaglandin E2 (PGE2), toll-like receptor 9 (TLR9), plasminogen (PLOD1), and SCL2A9 glucose transporter (SCL2A9).

7. The method of claim 1, wherein the one or more osteoarthritis biomarkers to be measured is selected from one or more of: a disintegrin and metallopeptidase with thrombospondin type 1 motif 4 (ADAMTS-4), interferon gamma (IFNG), hyaluronic acid synthase 2 (HAS2), biglycan (BGN), sex determining region Y-box 9 (SOX-9), a disintegrin and metallopeptidase with thrombospondin type 1 motif 5 (ADAMTS-5), acid phosphastase 5 (ACP 5), tenasin C (TNC), hyaluronic acid synthase 3 (HAS3), insulin-like growth factor 1 (IGF-1), ghrelin (GHR), X-prolyl dipeptidyl aminopeptidase (Xaa-Pro Peptidase), receptor activator of NF-Kappa B ligand (RANKL), mothers against decapentaplegic, drosophila, homolog of SMAD family member 7 (SMAD7), prostaglandin E2 (PGE2), toll-like receptor 9 (TLR9), plasminogen (PLOD1), and SCL2A9 glucose transporter (SCL2A9).

8. A method for treating an inflammatory condition in a canine, the method comprising:
detecting the inflammatory condition in the canine, wherein detecting the inflammatory condition comprises measuring decreased levels of one or more inflammatory biomarkers and increased levels of ANXA1 (Annexin A1) in blood of the canine as compared to healthy canines, and wherein the decreased levels of the one or more inflammatory biomarkers and the increased levels of ANXA1 (Annexin A1) in the blood indicate the presence of the inflammatory condition in tissue of the canine;
administering to the canine in need thereof a diet comprising, on a dry matter basis:
protein in an amount of 18-22%;
fat in an amount of 14.4-17.6%;
carbohydrates in an amount of 45.9-56.1%;
crude fiber in an amount of 8.1-9.9%;
DHA in an amount of 0.27-0.33%;
EPA in an amount of 0.45-0.55%;
vitamin C in an amount of 202.5-247.5 ppm;
vitamin E in an amount of 526.5-643.5 ppm; and
L-carnitine in an amount of 315.9-386.1 mg/kg; and
detecting a reduction in the inflammatory condition in the canine, wherein detecting the reduction in the inflammatory condition in the canine comprises measuring decreased levels of Annexin A1 (ANXA1) in the blood of the canine in need thereof as compared to the healthy canines, and wherein the decreased levels of the ANXA1 in the blood of the canine indicates the reduction in the inflammatory condition,
wherein the one or more osteoarthritis biomarkers to be measured is one or more of the group consisting of: interleukin 6 (IL-6), a disintegrin and metallopeptidase with thrombospondin type 1 motif 4 (ADAMTS-4), interferon gamma (IFNG), hyaluronic acid synthase 2 (HAS2), biglycan (BGN), sex determining region Y-box 9 (SOX-9), a disintegrin and metallopeptidase with thrombospondin type 1 motif 5 (ADAMTS-5), matrix metalloproteinase 3 (MMP3), acid phosphastase 5 (ACP5), interleukin 1A (IL1A), tenasin C (TNC), hyaluronic acid synthase 3 (HAS3), cartilage oligomeric matrix protein (COMP), insulin-like growth factor 1 (IGF-1), ghrelin (GHR), X-prolyl dipeptidyl aminopeptidase (Xaa-Pro Peptidase), receptor activator of NF-Kappa B ligand (RANKL), mothers against decapentaplegic, drosophila, homolog of SMAD family member 7 (SMAD7), prostaglandin E2 (PGE2), toll-like receptor 9 (TLR9), plasminogen (PLOD1), and SCL2A9 glucose transporter (SCL2A9).

9. The method of claim 8, wherein the one or more inflammatory biomarkers to be measured is selected from one or more of: interleukin 6 (IL-6), interferon gamma (IFNG), hyaluronic acid synthase 2 (HAS2), biglycan (BGN), sex determining region Y-box 9 (SOX-9), acid phosphastase 5 (ACP5), interleukin 1A (IL1A), tenasin C (TNC), hyaluronic acid synthase 3 (HAS3), insulin-like growth factor 1 (IGF-1), ghrelin (GHR), X-prolyl dipeptidyl aminopeptidase (Xaa-Pro Peptidase), receptor activator of NF-Kappa B ligand (RANKL), mothers against decapentaplegic, drosophila, homolog of SMAD family member 7 (SMAD7), prostaglandin E2 (PGE2), toll-like receptor 9 (TLR9), plasminogen (PLOD1), and SCL2A9 glucose transporter (SCL2A9).

* * * * *

UNITED STATES PATENT AND TRADEMARK OFFICE
CERTIFICATE OF CORRECTION

PATENT NO. : 10,564,169 B2
APPLICATION NO. : 13/642576
DATED : February 18, 2020
INVENTOR(S) : Nolan Zebulon Frantz Page 1 of 1

It is certified that error appears in the above-identified patent and that said Letters Patent is hereby corrected as shown below:

On the Title Page

Item (56), under "OTHER PUBLICATIONS", Line 34, delete "http:www." and insert -- http://www. --, therefor.

On Page 2, item (56), under "OTHER PUBLICATIONS", Line 20, delete "Medical." and insert -- Medical --, therefor.

In the Specification

In Column 3, Line 23, delete "neutered/ spayed" and insert -- neutered/spayed --, therefor.

Signed and Sealed this
Twenty-sixth Day of May, 2020

Andrei Iancu
*Director of the United States Patent and Trademark Office*